US008646311B1

United States Patent
Moseley

(10) Patent No.: US 8,646,311 B1
(45) Date of Patent: Feb. 11, 2014

(54) SENSORS FOR HYDROGEN, AMMONIA

(75) Inventor: Patrick T. Moseley, Durham, NC (US)

(73) Assignee: Atmospheric Sensors Ltd., Ely, Cambridgeshire (GB)

( * ) Notice: Subject to any disclaimer, the term of this patent is extended or adjusted under 35 U.S.C. 154(b) by 1501 days.

(21) Appl. No.: 12/290,478

(22) Filed: Oct. 31, 2008

Related U.S. Application Data

(60) Provisional application No. 61/002,500, filed on Nov. 9, 2007.

(51) Int. Cl.
*G01N 27/00* (2006.01)

(52) U.S. Cl.
USPC ........ 73/31.06; 73/29.01; 73/335.02; 422/83; 422/88; 422/98

(58) Field of Classification Search
USPC ........... 73/29.01, 335.02–335.05; 422/83, 90, 422/94
See application file for complete search history.

(56) References Cited

U.S. PATENT DOCUMENTS

| | | | |
|---|---|---|---|
| 3,932,246 A | 1/1976 | Stadler et al. | |
| 3,978,006 A | 8/1976 | Topp | |
| 4,015,230 A * | 3/1977 | Nitta et al. | 338/35 |
| 4,067,695 A | 1/1978 | Miyaguchi | |
| 4,226,692 A | 10/1980 | Isenberg | |
| 4,244,918 A | 1/1981 | Yasuda et al. | |
| 4,322,383 A | 3/1982 | Yasuda et al. | |
| 4,377,801 A | 3/1983 | Weber et al. | |
| 4,387,359 A | 6/1983 | Tien et al. | |
| 4,458,242 A | 7/1984 | Kusanagi et al. | |
| 4,579,751 A | 4/1986 | Forster | |
| 4,652,849 A | 3/1987 | Matsuura et al. | |
| 4,706,493 A | 11/1987 | Chang et al. | |
| 4,743,881 A | 5/1988 | Howng | |
| 4,952,904 A | 8/1990 | Johnson et al. | |
| 5,192,618 A | 3/1993 | Frankel et al. | |
| 5,460,710 A | 10/1995 | Williams et al. | |
| 5,497,808 A | 3/1996 | Schlund et al. | |
| 5,789,659 A | 8/1998 | Williams | |
| 5,811,662 A | 9/1998 | Williams et al. | |
| 5,814,281 A | 9/1998 | Williams et al. | |
| 5,856,780 A | 1/1999 | McGeehin | |
| 5,858,739 A | 1/1999 | Williams | |
| 5,893,892 A | 4/1999 | Loeffler | |
| 5,918,261 A | 6/1999 | Williams et al. | |
| 6,046,054 A | 4/2000 | McGeehin et al. | |
| 6,173,602 B1 | 1/2001 | Moseley | |
| 6,481,264 B1 | 11/2002 | Williams | |
| 6,660,231 B2 * | 12/2003 | Moseley | 422/98 |

(Continued)

*Primary Examiner* — In Suk Bullock
*Assistant Examiner* — Robert Eom
(74) *Attorney, Agent, or Firm* — James Creighton Wray

(57) ABSTRACT

A sensor for detecting hydrogen or ammonia gas uses a gas sensitive material based on $Cr_2O_3$ with a small percentage of the chromium replaced by transition metal ions having a valency greater than four, but still having a corundum crystal structure. Electrodes in contact with the gas sensitive material are connected by conductors to electrical measuring means for measuring the resistance, conductance, capacitance, or impedance of the gas sensitive material. A temperature sensing means and heating means allow the temperature of the gas sensitive material to be regulated. The gas sensitive material is formed on an insulator substrate over one or both electrodes. One electrode can be on the non-substrate side of the gas sensitive material. The gas sensitive material can be formed by deposition from a suspension or colloidal dispersion and firing. The gas sensitive material is contacted with gas and changes in electrical properties of the material are observed.

19 Claims, 1 Drawing Sheet

(56) References Cited

U.S. PATENT DOCUMENTS

| | | |
|---|---|---|
| 6,764,591 B1 | 7/2004 | Dutta et al. |
| 6,783,914 B1 | 8/2004 | Fedynyshyn |
| 6,993,955 B1 | 2/2006 | King et al. |
| 7,007,542 B2 | 3/2006 | Wang et al. |
| 7,010,957 B2 | 3/2006 | Williams et al. |
| 7,041,256 B2 | 5/2006 | Wang et al. |
| 7,300,640 B2 | 11/2007 | Ohtsuka et al. |
| 7,389,675 B1 | 6/2008 | Hunter et al. |
| 7,406,856 B2 | 8/2008 | Bottner et al. |
| 7,628,957 B1 | 12/2009 | Moseley et al. |
| 7,677,082 B2 | 3/2010 | Ramsier et al. |
| 2003/0048203 A1 | 3/2003 | Clary |
| 2008/0196478 A1 | 8/2008 | Raghurama |
| 2009/0283759 A1 | 11/2009 | Cole |
| 2010/0050744 A1 | 3/2010 | Petrovic |

\* cited by examiner

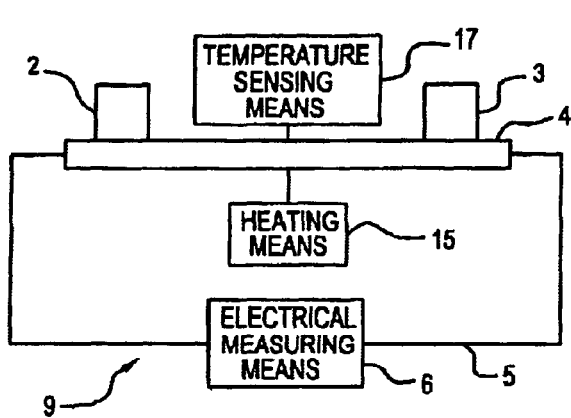
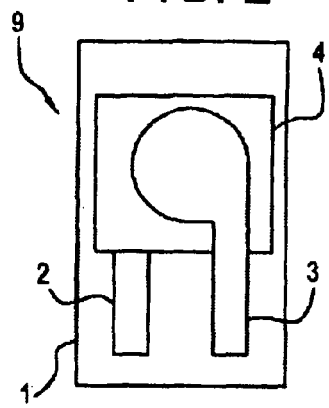
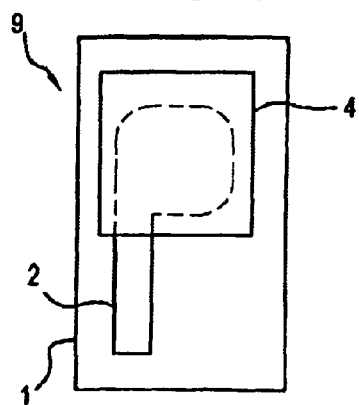
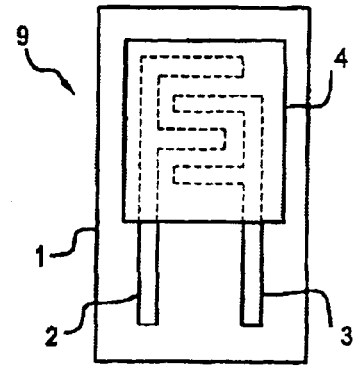

SENSORS FOR HYDROGEN, AMMONIA

This application claims the benefit of U.S. Provisional Application No. 61/002,500, filed Nov. 9, 2007, which is hereby incorporated by reference in its entirety.

BACKGROUND OF THE INVENTION

Semiconductor gas sensors operate by offering a change in electronic conductivity in response to a change in the concentration of a particular gas with which the sensors are in contact. A major challenge for such sensors is that they should be as selective as possible and not alter in resistance when exposed to common interferents such as a change in relative humidity.

A more subtle, although no-less important requirement is that the response that sensors offer to the intended target gas should arise through a single mechanism. In order that the response should be completed as rapidly as possible, it is desirable that the mechanism should operate at the surface of the active element: Bulk changes generally take place more slowly than do surface changes at any particular temperature.

A majority of semiconductor gas sensors produced in the world today employ tin dioxide as the active element, but this material suffers from a number of shortcomings including considerable cross-sensitivity and the need for an initial thermal "soak" in order to improve stability.

Another class of materials, based on the perovskite crystal structure is useful for monitoring oxygen (as shown in granted Patent GB 2,408,333) at high temperature but suffers from the concurrent operation of surface and bulk mechanisms when employed at lower temperature for the detection of reducing gases.

Needs exist for improved sensors, improved semiconductor gas sensors and improved materials for semiconductor gas sensors.

SUMMARY OF THE INVENTION

No attempt has previously been made to surmount the above difficulties by means of a ground-up creation of a material for a semiconductor gas sensor. The present invention describes and claims protection for a class of materials that have been created with this approach in mind.

Semiconducting oxides as used for gas sensing comprise two sub-lattices; one of oxygen ions, the other of metal ions. Since the oxygen ions are generally larger than the metal ions, the structures can be viewed as a 3-dimensional assembly of oxygen ions with the metal ions occupying interstices between them. The idealized materials should avoid the incorporation of soft, main group metal ions, as oxides of such metals tend to exhibit a pronounced susceptibility to a humidity response. Transition metal ions suffer less from this tendency. For the oxygen sub-lattice, it is important that there be no bulk vacancies. The perovskite structure tolerates a considerable proportion of oxygen vacancies. These allow oxygen ion mobility and are useful in the high temperature oxygen measurement. The bulk mobility of oxygen ions causes problems when the material is used at lower temperature for reducing gases because it introduces a slow process to the mechanism by which a resistance response occurs.

The present invention provides a structure with a close-packed assembly of oxygen ions for a good sensor material. The hexagonal close-packed array found in the corundum structure is ideal. This structure ideally has no oxygen vacancies and hence offers negligible oxygen ion mobility. The regular corundum structure has 3-valent metal ions sited in interstices within the oxygen sub-lattice. If these metal ions are aluminum, the material is an insulator. If the metal ions are, for the most part, chromium ions, then the structure can be invested with suitable electronic and catalytic properties by the inclusion of a small percentage of transition metal ions with a higher valency to complete the cation inventory. This allows good p-type conductivity combined with surface gas-sensitivity.

If the minority cation is titanium, then a material with sensitivity to carbon monoxide and hydrogen sulfide is produced. However, the same number of essential charge carriers can be introduced by using a smaller amount of transition metal dopants, if those dopants carry a valence higher than that carried by titanium (i.e. 4). Such high-valence dopants may constitute, for example, 0.1% to 5% of the material, leaving 95% to 99.9% $Cr_2O_3$. Frequently, 0.5% to 1% dopant achieves good results. The exact composition may be optimized to seek the maximum response for a given application. The lower degree of substitution allowed by using metal ions of 5- or 6-valency contributes to enhancing the stability of the product. Further, some of the transition metals that characteristically exhibit higher valency than does titanium also tend to have better catalytic properties than titanium, and this is important for gas sensitivity.

Hence materials based on $Cr_2O_3$ with a small percentage of the chromium replaced by niobium or tungsten but still having the corundum crystal structure have good properties for sensing hydrogen and ammonia in air. $Cr_2O_3$ containing a small amount of molybdenum, but still retaining the corundum structure, offers similar useful properties.

The new crystal structure and composition is purpose-created for the sensing of hydrogen or ammonia in air. The crystal structure is based on the close-packed assembly of oxygen ions, as in the crystal structure of corundum, with most of the cation sites occupied by chromium and the rest occupied by niobium or tungsten or molybdenum.

A new sensor apparatus for sensing hydrogen or ammonia in air includes a gas sensitive material based on $Cr_2O_3$ with a small percentage of the chromium replaced by transition metal ions having a valency greater than three, but still having a corundum crystal structure, and first and second electrodes in contact with the gas sensitive material. In one embodiment, the sensor apparatus also includes an electrical measuring means for measuring resistance, conductance, capacitance, or impedance, and conductors connecting the electrodes to the electrical measuring means. A temperature sensing means and a heating means may be connected to the gas sensitive material for heating the sensor.

The transition metal ions having a valency greater than three may be niobium, tungsten, or molybdenum ions. The transition metal ions having a valency greater than three may make up 0.1% to 5% of the gas sensing material by mass.

In one embodiment, an insulating substrate may carry the gas sensitive material. Part of the first electrode may be between the substrate and the gas sensitive material and the second electrode may be on the opposite side of the gas sensitive material from the first electrode. Part of the first electrode and part of the second electrode may alternatively be between the substrate and the gas sensitive material and not overlap, and the portions of the first and second electrodes between the substrate and the gas sensitive material may be interdigitated.

In a new method for producing a sensor apparatus for sensing hydrogen or ammonia in air, an insulating substrate is provided, a first electrode is applied to the insulating substrate, a layer of gas sensitive material is formed over a portion of the first electrode and insulating substrate, and a second electrode is applied. The gas sensitive material is based on $Cr_2O_3$ with a small percentage of the chromium replaced by transition metal ions having a valency greater than three, but still having a corundum crystal structure. An electrical measuring means may be provided for measuring resistance, conductance, capacitance, or impedance, and conductors may be provided connecting the first and second electrodes to the electrical measuring means.

In one embodiment, in applying a second electrode, part of the second electrode may be applied on the layer of gas sensitive material. In another embodiment, in applying a second electrode, the second electrode may be applied on the substrate before the layer of gas sensitive material is formed. In applying a second electrode, the first and second electrodes may be interdigitated.

In forming a layer of gas sensitive material, the layer of gas sensitive material may be formed by deposition from a suspension or colloidal dispersion and firing. The firing may be done at a temperature in the range of 450-900° C. The firing may be done at a temperature in the range of 450-700° C. The deposition may include screen printing or doctor blading. Applying the first or second electrode may include screen printing or sputtering.

In a new hydrogen or ammonia gas sensing method, a hydrogen or ammonia gas sensor is provided and includes a gas sensitive material based on $Cr_2O_3$ with a small percentage of the chromium replaced by transition metal ions having a valency greater than three, but still having a corundum crystal structure, and first and second electrodes connected by conductors to an electrical measuring means for measuring resistance, conductance, capacitance, or impedance. The hydrogen or ammonia gas sensor is contacted with a gas or gaseous mixture and the resistance, conductance, capacitance, or impedance of the gas sensitive material is measured with the electrical measuring means.

These and further and other objects and features of the invention are apparent in the disclosure, which includes the above and ongoing written specification, with the claims and the drawings.

BRIEF DESCRIPTION OF THE DRAWINGS

FIG. 1 is a diagrammatic representation of one form of a sensor in accordance with the present invention.

FIGS. 2 and 3 represent diagrammatically a parallel plate sensor in accordance with the present invention and a partially completed parallel plate sensor respectively.

FIG. 4 is a diagrammatic representation of a coplanar sensor in accordance with the present invention.

DETAILED DESCRIPTION OF THE DRAWINGS

FIG. 1 shows a sensor 9 comprising a gas sensitive material 4 and, in contact with the gas sensitive material, gold electrodes 2 and 3. The gas sensitive material may be carried by a substrate (e.g. of alumina) (not shown).

Conductors 5 are provided to connect the electrodes 2 and 3 respectively to electrical measuring means 6 for measuring the resistance and/or capacitance and/or impedance of the gas sensitive material 4. Any type of electrical measuring means may be used, including a meter or circuit.

In operation a gas or gaseous mixture is contacted with the gas sensitive material 4.

The resistance and/or conductance and/or impedance is measured by the electrical measuring means 6. Changes in the composition of the gas or gaseous mixture which result in a change of resistance and/or conductance and/or capacitance and/or impedance are observed as changes in the resistance and/or conductance and/or capacitance and/or impedance recorded by the measuring means 6. Sensor 9 may include temperature sensing means 17 for sensing temperature and heating means 15 for heating the sensor.

Any type of temperature sensing means and heating means may be used, such as an electric resistance heater with resistance sensor. For example, a platinum heater may be used as a heating means. The platinum may be provided as a thick film printed heater track on the underside of the sensor and current passed through the platinum until it reaches a desired temperature. By detecting the resistance of the platinum, which changes with temperature, it can also function as a temperature sensing means. Platinum is a preferred choice for a temperature sensing material because it has a well known temperature coefficient of resistance, however other materials could also be used.

FIG. 2 shows an insulating substrate 1 (e.g. an alumina ceramic tile) upon which is formed a first electrode 2 (e.g. of gold), a gas sensitive material layer 4 comprising a gas sensitive material in accordance with the present invention and a second electrode 3 (e.g. of gold).

A parallel plate sensor 9, as shown in FIG. 2, may be fabricated by applying the first electrode 2 (e.g. of gold) to the insulating substrate 1 (e.g. by screen printing or sputtering), forming a gas sensitive material layer 4 by deposition, for example by screen printing or doctor blading, from a suspension or a colloidal dispersion and firing at a temperature in the range 450.degree.-900.degree. C. to promote adhesion and mechanical integrity and forming a second electrode 3 (e.g. of gold) on the gas sensitive material layer 4, (e.g. by screen printing or sputtering).

In order to facilitate understanding of the construction of the sensor of FIG. 2 reference may be made to FIG. 3, which shows a parallel plate sensor 9 of the type shown in FIG. 2 partially completed inasmuch as the second electrode 3 has not been formed. FIG. 3 thus shows the insulating substrate 1, the first electrode 2 and the gas sensitive material layer 4 and it is seen that the portion of the first electrode 2 covered by the gas sensitive material layer 4 may preferably extend in area to substantially the same extent as the second electrode 3.

In operation, the first electrode 2 and second electrode 3 are connected to an electrical measuring means (not shown) for measuring the resistance and/or capacitance and/or impedance of the gas sensitive material layer 4 and the sensor is contacted with a gas or gaseous mixture. The resistance and/or capacitance and/or impedance is measured by the electrical measuring means and changes in the composition of the gas or gaseous mixture which result in a change of resistance and/or capacitance and/or impedance are observed as changes in the resistance and/or capacitance and/or impedance recorded by the electrical measuring means.

FIG. 4 shows an insulating substrate 1 (e.g. an alumina ceramic tile) upon which are formed electrodes 2 and 3 (e.g. both of gold), and a gas sensitive material layer 4 comprising a gas sensitive material in accordance with the present invention. It is seen from the lines shown in dotted form in FIG. 4 that the portions of the first electrode 2 and second electrode 3 covered by the gas sensitive material layer 4 are interdigitated.

The first electrode 2 and the second electrode 3 may be provided on the insulating substrate 1 by any suitable method. For example, the methods disclosed for providing electrodes 2 and 3 in the parallel plate sensor, described with reference to FIG. 2 and FIG. 3, may be used.

The gas sensitive material layer 4 shown in FIG. 4 may be prepared by any suitable method. For example, the methods disclosed for preparing gas sensitive material layer 4 in FIG. 2 and FIG. 3 may be used.

While the invention has been described with reference to specific embodiments, modifications and variations of the invention may be constructed without departing from the scope of the invention, which is defined in the following claims.

I claim:

1. A sensor apparatus for sensing hydrogen or ammonia in air, comprising
    a hydrogen and ammonia gas sensitive material based on $Cr_2O_3$, wherein a small percentage of chromium cation sites in the $Cr_2O_3$ are replaced and occupied by transition metal ions having a valency greater than four, but still having a corundum crystal structure,
    first and second electrodes in contact with the gas sensitive material, and wherein
    the transition metal ions having a valency greater than four are selected from the group consisting of tungsten ions and molybdenum ions.

2. The sensor apparatus of claim 1, further comprising an electrical measuring means for measuring resistance, conductance, capacitance, or impedance, and conductors connecting the electrodes to the electrical measuring means.

3. The sensor apparatus of claim 1, further comprising a temperature sensing means and a heating means connected to the gas sensitive material for heating the sensor.

4. The sensor apparatus of claim 1, wherein the transition metal ions having a valency greater than four make up 0.1% to 5% of the gas sensing material by mass.

5. The sensor apparatus of claim 1, further comprising an insulating substrate carrying the gas sensitive material.

6. The sensor apparatus of claim 5, wherein part of the first electrode is between the substrate and the gas sensitive material and the second electrode is on the opposite side of the gas sensitive material from the first electrode.

7. The sensor apparatus of claim 5, wherein part of the first electrode and part of the second electrode are between the substrate and the gas sensitive material and do not overlap, and wherein the portions of the first and second electrodes between the substrate and the gas sensitive material are interdigitated.

8. A method for producing a sensor apparatus for sensing hydrogen or ammonia in air, comprising
    providing an insulating substrate,
    applying a first electrode to the insulating substrate,
    forming a layer of gas sensitive material over a portion of the first electrode and insulating substrate, and
    applying a second electrode,
    wherein the gas sensitive material is based on $Cr_2O_3$, wherein a small percentage of chromium cation sites in the $Cr_2O_3$ are replaced and occupied by transition metal ions having a valency greater than four, but still having a corundum crystal structure, and wherein
    the transition metal ions having a valency greater than four are selected from the group consisting of tungsten ions and molybdenum ions.

9. The method for producing a sensor apparatus of claim 8, further comprising providing an electrical measuring means for measuring resistance, conductance, capacitance, or impedance, and
    providing conductors connecting the first and second electrodes to the electrical measuring means.

10. The method for producing a sensor apparatus of claim 8, wherein the applying a second electrode comprises applying part of the second electrode on the layer of gas sensitive material.

11. The method for producing a sensor apparatus of claim 8, wherein the applying a second electrode comprises applying the second electrode on the substrate before the layer of gas sensitive material is formed.

12. The method of producing a sensor apparatus of claim 11, wherein the applying a second electrode comprises interdigitating the first and second electrodes.

13. The method for producing a sensor apparatus of claim 8, wherein forming a layer of gas sensitive material comprises forming the layer of gas sensitive material by deposition from a suspension or colloidal dispersion and firing.

14. The method for producing a sensor apparatus of claim 13, wherein the firing is done at a temperature in the range of 450-900° C.

15. The method for producing a sensor apparatus of claim 13, wherein the firing is done at a temperature in the range of 450-700° C.

16. The method for producing a sensor apparatus of claim 13, wherein the deposition comprises screen printing or doctor blading.

17. The method for producing a sensor apparatus of claim 8, wherein applying the first or second electrode comprises screen printing or sputtering.

18. A hydrogen or ammonia gas sensing method, comprising
    providing a hydrogen or ammonia gas sensor comprising a gas sensitive material based on $Cr_2O_3$, wherein a small percentage of chromium cation sites in the $Cr_2O_3$ are replaced and occupied by transition metal ions having a valency greater than four, but still having a corundum crystal structure, and first and second electrodes connected by conductors to an electrical measuring means for measuring resistance, conductance, capacitance, or impedance,
    contacting the hydrogen or ammonia gas sensor with a gas or gaseous mixture, and
    measuring the resistance, conductance, capacitance, or impedance of the gas sensitive material with the electrical measuring means, and wherein
    the transition metal ions having a valency greater than four are selected from the group consisting of tungsten ions and molybdenum ions.

19. A sensor apparatus for sensing hydrogen or ammonia in air, comprising
    an insulating substrate,
    a first electrode to the insulating substrate,
    a layer of gas sensitive material over a portion of the first electrode and insulating substrate, and
    a second electrode in contact with the gas sensitive material,
    wherein the gas sensitive material is based on $Cr_2O_3$, wherein a small percentage of chromium cation sites in the $Cr_2O_3$ are replaced and occupied by transition metal ions having a valency greater than four, but still having a corundum crystal structure, and wherein
    the transition metal ions having a valency greater than four are selected from the group consisting of tungsten ions and molybdenum ions.

* * * * *